(12) United States Patent
Jarvis

(10) Patent No.: US 9,794,986 B2
(45) Date of Patent: Oct. 17, 2017

(54) THERMAL BATH WITH OBLONG POLISHED METAL PELLETS

(75) Inventor: Richard A Jarvis, San Antonio, TX (US)

(73) Assignee: Lab Armor, LLC, Cornelius, OR (US)

( * ) Notice: Subject to any disclaimer, the term of this patent is extended or adjusted under 35 U.S.C. 154(b) by 1596 days.

(21) Appl. No.: 13/410,288

(22) Filed: Mar. 1, 2012

(65) Prior Publication Data

US 2012/0216994 A1 Aug. 30, 2012
US 2016/0323935 A9 Nov. 3, 2016

Related U.S. Application Data

(63) Continuation-in-part of application No. 12/381,102, filed on Mar. 6, 2009, now abandoned.

(60) Provisional application No. 61/068,505, filed on Mar. 7, 2008.

(51) Int. Cl.
| | |
|---|---|
| *C09K 5/14* | (2006.01) |
| *H05B 1/02* | (2006.01) |
| *A01N 25/34* | (2006.01) |

(52) U.S. Cl.
CPC ........... *H05B 1/0213* (2013.01); *A01N 25/34* (2013.01); *C09K 5/14* (2013.01)

(58) Field of Classification Search
None
See application file for complete search history.

(56) References Cited

U.S. PATENT DOCUMENTS

| | | | |
|---|---|---|---|
| 182,329 A | * | 9/1876 | Poole ................. B01F 9/06 144/208.9 |
| 1,378,474 A | | 5/1921 | Lidberg |
| 2,644,799 A | | 7/1953 | Robinson |
| 3,478,745 A | | 11/1969 | De |

(Continued)

FOREIGN PATENT DOCUMENTS

WO   WO 98/55093   * 12/1998

OTHER PUBLICATIONS

University of Ottawa, Biosafety Manual (Mar. 7, 2003), pp. 1-40, retrieved from internet URL http://www.uottawa.ca/services/ehss/docs/biosafety-manual.pdf on Mar. 9, 2010.*

(Continued)

*Primary Examiner* — Yelena G Gakh
*Assistant Examiner* — Michelle Adams
(74) *Attorney, Agent, or Firm* — William H. Quirk; Jesse Frizzell; Rosenthal Pauerstein Sandoloski Agather LLP

(57) ABSTRACT

Systems and methods for controlling the temperature of items such as a sample in a vessel or a specimen, in a thermal bath using thermally efficient pellets as the thermal media. The pellets are typically oblong metallic or oblong metallic-coated pellets with rounded edges, a hardened surface, a smooth polished finish, and characteristics that enable efficient thermal communication between the bath's thermal source, the pellets, and the items that are inserted into the mass of pellets. Further, the pellets are dry and moisture and gas impermeable, and they resist microbial growth and are readily decontaminated by several methods including applying an antimicrobial compound to the pellets. The thermal source is controlled to achieve the desired temperature of the items inserted into the pellets.

13 Claims, 3 Drawing Sheets

(56) References Cited

U.S. PATENT DOCUMENTS

| | | | | |
|---|---|---|---|---|
| 4,054,376 A * | 10/1977 | Wareham | ............... | G02C 13/00 |
| | | | | 165/104.16 |
| 4,758,285 A * | 7/1988 | Hodgson | .................. | C21D 8/00 |
| | | | | 148/563 |
| 4,809,771 A | 3/1989 | Kennel et al. | | |
| 4,896,023 A * | 1/1990 | Uchiyama | ................ | A61L 2/04 |
| | | | | 219/242 |
| 5,286,951 A * | 2/1994 | Jones | ....................... | B23Q 3/08 |
| | | | | 165/104.16 |
| 5,396,049 A * | 3/1995 | Knopf | ....................... | A61L 2/04 |
| | | | | 219/385 |
| 6,263,958 B1 | 7/2001 | Fleishman | | |
| 7,124,809 B2 * | 10/2006 | Rosenfeld et al. | ...... | 165/104.26 |
| 2005/0252636 A1* | 11/2005 | Kauppila et al. | ............... | 165/47 |
| 2006/0240122 A1* | 10/2006 | Miner | .................... | C11D 3/046 |
| | | | | 424/618 |
| 2009/0233375 A1* | 9/2009 | Jarvis | ........................... | 436/151 |

OTHER PUBLICATIONS

Fernando Sanford (1902) "Elements of Physics," New York: Henry Holt and Company, p. 186.*
"Sand Bath", Wikipedia, Jan. 13, 2008, Retrieved from Internet: http://en.wikipedia.org/w/index.php?title=Sand_bath&oldid=183981903.
Major Science, Online Catalogue, Metallic Thermal Beads. http://www.majorsci.com/9-4-MX-Beads.html. Aug. 5, 2014. pp. 1-2 (Presumably published in 2014).

* cited by examiner

THERMAL BATH WITH OBLONG POLISHED METAL PELLETS

CROSS REFERENCES TO RELATED APPLICATION

The present application claims benefit of and is a continuation-in-part of Non-Provisional U.S. patent application Ser. No. 12/381,102, filed Mar. 6, 2009 (the "Parent Application"), and also claims the benefit of U.S. Provisional Application No. 61/068,505, filed Mar. 7, 2008 (the "Provisional Foundation"), to which the Parent Application claims priority. By this reference, the full disclosures of the Parent Application and its Provisional Foundation, including the claims and drawings of each of the above identified applications, are incorporated herein as though now set forth in their entirety.

BACKGROUND OF THE INVENTION

Field of the Invention

The present invention relates to thermal instrument baths. More particularly, it especially relates to laboratory thermal baths and media for use therein to provide instrument maintenance and microbial contamination control benefits.

Related Art

Laboratory thermal baths such as water baths and dry blocks are well-established laboratory instruments for heating or cooling objects, vessels, or samples contained therein. Laboratory thermal baths comprise a thermal source, a temperature control unit, power source, insulation, and a tub to contain wet or dry thermal tub media. Thermal bath media such as water or drilled out aluminum blocks have become a standard practice in the laboratory.

One drawback to the present thermal bath media is that laboratory thermal baths are generally set at temperatures ideal for biological activity, and therefore can promote the growth of invading microorganisms on or within the media, including bacteria, yeast, fungi, and virus. This can place laboratory personnel at risk, compromise laboratory supplies and equipment, jeopardize sterile operations, and require substantial routine instrument cleaning and maintenance. Wet thermal bath media, in particular water, is usually treated with antibiotic agents to prevent the initiation and persistence of contamination. However, these agents are impermanent, and without rigorous maintenance and regular renewal, they become less effective. Moreover, these agents can contribute to the formation of antibiotic resistant biofilms. Such biofilms comprised of *Escherichia coli, staphylococcus*, or other microorganisms responsible for difficult-to-treat infections in humans, pose a significant risk to personnel and patients in laboratories and healthcare facilities. Furthermore, objects or capped or uncapped vessels containing samples that are placed into the water of the laboratory thermal bath are prone to tipping over and floating. Such events can lead to the contamination or destruction of costly samples or sample contamination of the thermal bath and the laboratory. Moreover, thermal baths require frequent water replenishment and routine cleaning and maintenance, which can be time-consuming and costly.

Conventional dry thermal bath media reduce risks associated with water but have several additional drawbacks. In particular, solid aluminum block systems limit the vessels that can be used to the size and shape of the drilled-out receptacles in their bodies. Laboratory vessels due to their unique size or shape usually necessitate the purchase of numerous aluminum blocks or the costly production of custom aluminum block systems. Drawbacks to considering the use of more particulate dry thermal bath media include performance challenges to minimizing the bioburden of the bath and optimizing the ability to support bathed objects in an optimally stable position, while also providing effective thermal transfer properties. The characteristics of particulate matter impact the raw material cost as well as the cost and ease of using, handling, and processing the particulate matter for any particular application.

Many other objects and advantages will be evident to one of ordinary skill in the art. In view of the further descriptions herein, especially considered in light of the prior art, it is therefore yet another object of the present invention to improve upon, and overcome the obstacles of the prior art.

BRIEF SUMMARY OF THE INVENTION

The present invention provides thermal bath media capable of maintaining a relatively constant temperature, having optimal shape and size, and maintenance and contamination control benefits. Central to many aspects of the present invention is thermally-conductive particulate media distinguished from conventional thermal bath media. Some of the most favorable qualities of the thermally-conductive particulate media is appreciated with media in the form of smooth, oblong pellets having their widest dimension between two and thirty millimeters, wherein said materials are capable of providing thermal transfer when used in standard laboratory thermal bath. In particular, the thermally-conductive pellets are non-granular and not jagged so as not to pierce or puncture objects inserted into them, and are moisture and gas impermeable to prevent the harboring of contaminants, and are sufficiently smooth, stiff and incompressible, and in some instances are sufficiently elliptical but noncircular in at least one cross-section to permit easy insertion of vessels to promote efficient thermal transfer. The media may comprise pellets having a mixture of uniform or non-uniform shapes and sizes.

The materials of the thermally-conductive particulate media can be a metal, preferably aluminum, silver, or copper, or a plastic, or graphite, or the like, typically shaped like pea gravel or slightly-flattened jelly-filled doughnuts. The materials can be molded or can be in the form of raw manufacturing material. The materials can comprise a polished, plated, or otherwise coated surface to provide a desired finish. The pellets may comprise an outer surface and a core, wherein the outer surface material is different from the core materials or the core may be substantially hollow.

The materials of the thermally-conductive pellets are dry and naturally more resistant to microbial growth and than water and therefore less likely to harbor and contribute to transmitting microorganisms in the laboratory. Microbial growth can be further diminished by autoclaving or by routinely applying antimicrobial agents such as fungicides, algaecides virucides, and bactericides to the thermally-conductive pellets. Such antimicrobial agents can be permanently incorporated into the thermally-conductive pellets or otherwise onto the thermally-conductive pellets as a coating. Such coatings can prevent hazardous biofilm formation and produce a microbial contamination barrier. Examples of antimicrobial coatings include solutions comprised of ionic silver, ionic copper, or any permanent or semi-permanent disinfectant.

A further advantage of the thermally-conductive pellets hereof over conventional dry thermal bath media comprised of drilled out aluminum blocks is the ability of the pellets to conform to varied sizes and shapes of vessels placed in the laboratory thermal tub. The thermally-conductive pellets fill around the vessel providing sufficient thermal communication between the pellets and the vessel, thereby allowing the vessel and its contained specimen to reach the intended temperature.

Embodiments of various other aspects of the present invention also include a thermal control system comprising a laboratory thermal bath and media of thermally-conductive pellets contained in said bath and a method for inserting sample vessels into the media in thermal communication with the bath.

DETAILED DESCRIPTION OF PREFERRED EMBODIMENTS

Figure 1:
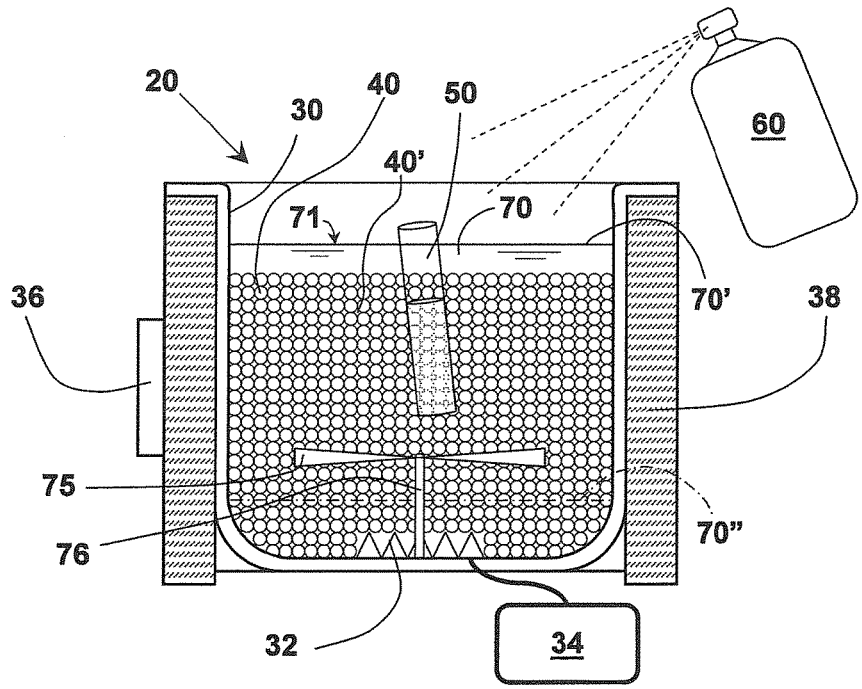
FIG. 1 is a partially-cross-sectional schematic representation of one preferred embodiment of a thermal bath system (20) according to the teachings of the present invention.

Referring now to preferred embodiments in more detail, FIG. 1 shows a partially-cross-sectional schematic representation of a thermal bath system (20) according to the teachings of the present invention. On the basic level, laboratory thermal bath system (20) comprises many components similar to those of conventional laboratory thermal bath systems—namely a tub (30), a thermal source (32), power source (34), a temperature control unit (36), and thermal insulation (38). Conventional laboratory thermal baths such as water baths and dry blocks are well-established laboratory instruments for heating or cooling objects, vessels, or samples contained therein, and their uses have become standard practices in the laboratory. Hence, as will be evident to those of ordinary skill in the art, various alternative embodiments of the certain aspects of the present invention can be implemented by use and/or modification of virtually any conventional laboratory thermal bath systems and their components. Such conventional laboratory thermal baths can be obtained from numerous manufacturers through a variety of sources—Fisher Scientific, VWR Scientific, Neslab, Tecam, and Applied Thermal Control, to name a few.

Thermal bath system (20) of FIG. 1 combines such conventional elements together with particulate thermally-conductive media (40) and, preferably, a disinfectant (60), to provide an overall laboratory thermal bath system (20) that can be employed to statically support and control the temperature of specimens such as sample vessel (50). The tub (30) is a conventional tub that is typically employed to contain liquid thermal tub media, although modifications or substitutions may be made when using dry media without a liquid phase, as will be evident to those of skill in the art. In the embodiment of FIG. 1, tub (30) is capable of containing thermally-conductive particulate media (40) (as described further herein). The particulate media preferably includes thermally-conductive particles (40) that are referred to herein as "pellets," although their preferred shapes (described further herein) are typically more like pea gravel or slightly-flattened jelly-filled doughnuts. The particulate media serves principally to communicate thermal energy between thermal source (32) and specimen vessel (50). The particulate nature of media (40) secondarily serves to support one or more vessel(s) (50) in a static orientation within media (40). Such static support helps keep vessels (50) biased in an upright orientation over time rather than dumping over and risking contamination. The static support of particulate media (40) also helps keep multiple vessels (50) in order within tub (30) to avoid confusion and for better tracking and the like.

In use of the embodiment of FIG. 1 (and the alternative embodiments described herein), one or more specimen vessels (50) are inserted into the particulate media (40) through the upper opening of the tub (30). Although the specimen vessel (50) in the illustrated embodiment is a single test tube containing a liquid specimen, system (20) may be used for affecting or maintaining the thermal state of any form of specimen and/or specimen vessel for which laboratory thermal control is desired. Such specimens and/or specimen vessels may include solid objects or any form of laboratory vessel, including (without limitation) test tubes, vials, beakers, bottles, slides, bags and the like, and the contents contained thereby. As will be described further herein in connection with FIG. 11, laboratory thermal bath system (20) can be employed for heating or cooling one or more sample vessels (50) positioned in the thermally-conductive particulate media (40) contained therein.

In the embodiment of FIG. 1, the temperature of the media (40) and consequently the specimen vessel (50) is maintained by insulation (38) in the body walls of tub (30) and by thermal source (32) typically located at the base of tub (30). Although alternatives may be substituted, thermal source (32) is powered by an electrical power supply (34) and controlled by thermal control unit (36). The thermal control unit (36) is preferably of the type having a temperature sensor and a microprocessor that can be programmed or mechanical dials that can be electronically set and executed.

The illustrated disinfectant (60) is a spray disinfectant that is periodically sprayed into media (40) in sufficient amounts to disinfect the surfaces of pellets (40). When practical, the pellets (40) are stirred in the course of applying the spray disinfectant (60) in order to increase the contact of the sprayed disinfectant with substantially all surfaces of the pellets (40). One particular preferred embodiment of disinfectant (60) is a spray bottle of silver dihydrogen citrate, a broad-spectrum antimicrobial disinfectant, which confers further advantages to the thermally-conductive pellets (40). The disinfectant (60) when used to treat the thermally-conductive pellets (40) can destroy existing harmful microbes and prevent the growth and spread of new microbes in the laboratory. Alternative disinfectants such as bleach, alcohols, ammonium derivatives, or others can be substituted with corresponding properties and benefits. For each alternative of the sprayed form of disinfectant (60), care is taken to ensure that the disinfectant (60) does not enter within the vessel (50), in order to avoid deleterious affects on the specimen therein.

Other alternatives for certain embodiments of the present invention include forms of disinfectant (60) that are not spray disinfectants. For instance, in embodiments of the invention when the spray character is not critical, disinfectant (60) may be in the form of disinfectant films, layers, coatings or impregnations that are either integral with pellets (40) or otherwise disposed in contact with the outer surfaces of pellets (40), or may be in the form of process controls such as high temperature treatment, autoclaving, washing, or mechanical treatment. One particularly preferred washing system is a flow-through system that disinfects pellets (40) by circulating a liquid disinfectant through the media (40) while the media (40) is in its operative place within tub (30). Variations on such flow-through systems can be adapted to utilize steam, ethylene oxide (EtO) or other gaseous disinfectants as well, although some additional adaptations will be required to handle the gas, as will be evident to those of skill in the art. Many other alternative disinfectants will be evident to those of skill in the art, with corresponding benefits and detractions from the foregoing embodiments.

With reference to FIG. 2 through FIG. 7, variously-shaped alternative embodiments (41-49) of thermally-conductive pellets (40) have substantially rounded edges and hardened surfaces with a smooth polished finish. The rounded edges and polished surfaces of pellets (41-49) make the pellets smooth and are each adaptations to ensure that, when sample vessels (50) are placed into the tub (30) to be warmed or cooled or whenever the vessels (50) are manually moved around within tub (30), adjacent pellets (40) exert minimal friction against each other. Hence, the smooth pellets (40) move fluidly relative to each other to surround the vessel (50) with minimal frictional resistance and without significantly risking scratching of the surfaces of the vessels (50), which are typically glass or plastic surfaces. The thermally-conductive pellets (41-49), when used as media (40) in a thermal tub (30), fill sufficiently deep so that vessels (50) placed into the tub (30) are sufficiently submerged in the media (40). When tub (30) is so filled with particulate media (40), the sample vessels (50) are held in place and in position without the need for a further holding device, such as stationary or floating racks.

Figure 2:
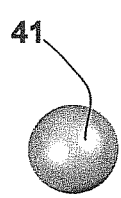
FIG. 2 is a side view of a spherical thermally-conductive pellet (41) of certain embodiments of the present invention.
Figure 3:
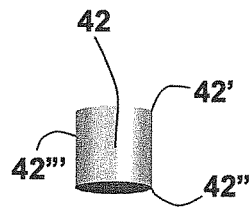
FIG. 3 is a side perspective view of a cylindrically-shaped thermally-conductive pellet (42) of certain embodiments of the present invention.
Figure 4:
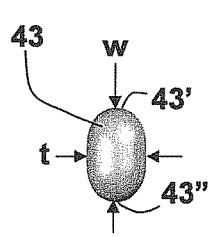
FIG. 4 is a side view of a prolately-shaped thermally-conductive pellet (43) of certain embodiments of the present invention.

The different shapes of pellets (41-49) provide different benefits and detractions of the various embodiments that can be used for particulate media (40) of the present invention. Some aspects of the present invention are embodied with the use of oblong pellets, such as is described further herein. Although a spherical thermally-conductive pellet (41) as shown in FIG. 2 is not oblong, some aspects of the present invention can be appreciated with the use of pellets (41) having a spherical shape, either alone or in combination with oblong pellets (40). Likewise, although a cylindrical thermally-conductive pellet (42) as shown in FIG. 3 has some edges (42' & 42") that are not rounded, its sidewall (42") is rounded, and some aspects of the present invention can be appreciated with the use of pellets (42) that have some non-rounded edges (42' & 42"), either alone or in combination with pellets (40) that have all their surfaces and edges rounded.

Figure 6:
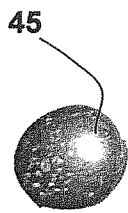
FIG. 6 is a perspective view of five sample pellets (45-49) representing a particularly preferred embodiment of oblong variations of pellets (40) of the present invention.
Figure 6:
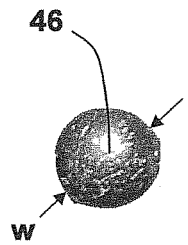
Figure 6:
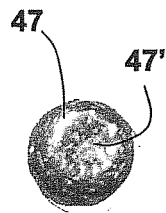
Figure 6:
Figure 6:
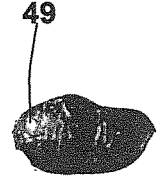
Figure 7:
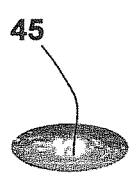
FIG. 7 is an orthogonal view of the pellets (45-49) of FIG. 6.
Figure 7:
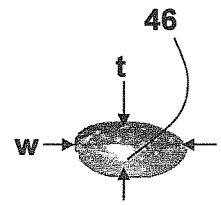
Figure 7:
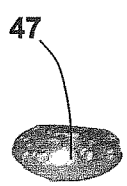
Figure 7:
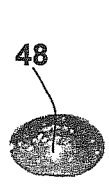
Figure 7:
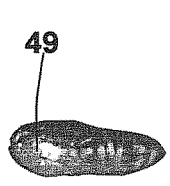

It may be that surface descriptions such as "rounded," "polished" and "smooth" may be thought of as relative terms. It should be understood that pellets (40) can have immaterial surface imperfections (such as the imperfections visible in FIGS. 6 & 7) while still being considered "rounded" and "smooth." All of the surfaces and edges of the pellets (45-49) shown in FIGS. 6 and 7 are considered rounded and smooth despite all the imperfections visible therein. While the "polished" term refers to the way the surface of a pellet (40) is processed, all the surfaces of the pellets (45-49) shown in FIGS. 6 and 7 are polished. It is also noted that concavities in the surface of a pellet (40), such as the central dimple (47') of the middle pellet (47) in FIG. 6, are immaterial to smoothness of the pellet (40). In an attempt to quantify the size of immaterial surface protrusions from an otherwise smooth surface, it is thought that surface protrusions having protruding dimensions (i.e., the radial extent of the protrusion) that are less than a third of the thinnest dimension (t) of an otherwise smooth pellet (40) are immaterial. Despite such protruding imperfections, it is thought that protrusions of such sizes would still be smooth.

Figure 5:
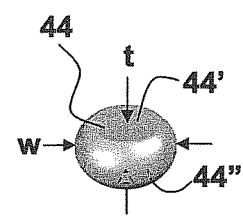
FIG. 5 is a perspective view of an oblately-shaped thermally-conductive pellet (44) of certain embodiments of the present invention.

The pellets that make up at least the bulk (i.e., the majority by volume) if not the entirety of particulate media (40) in tub (30) are preferably oblong pellets. Referring particularly to the pellets (43 & 44) of FIGS. 4 & 5, the shape of oblong pellets can be better understood. Such pellets are referred to as "oblong" in the sense that each pellet's (43, 44) shortest through dimension (its "thinnest dimension" or "t") is significantly shorter than its longest through dimension (its "widest dimension" or "w"). The prolately-shaped pellet (43) of FIG. 4 more accurately has the shape of a vertical cylinder with hemi-spherically rounded ends (43' & 43"); the thinnest dimension (t) of pellet 43 being the thickness of the cylinder, and the widest dimension (w) being the distance between the ends (43' & 43"). The prolately-shaped pellet (44) of FIG. 5 more accurately has the shape of a prolate sphere (or an ellipsoid, much like the globe of the Earth) with symmetrically-truncated polar ends (44' & 44"); the widest dimension (w) of pellet (44) being the equatorial diameter of the prolate sphere, and the thinnest dimension (t) being the distance between the truncated polar ends (43' & 43"). Both the prolately-shaped pellet (43) of FIG. 4 and the oblately-shaped pellet (44) of FIG. 5 are oblong.

Preferably, an oblong pellet of particulate media (40) has a thinnest dimension (t) that is about half of its widest dimension (w) or, preferably, more than 25% and less than 75% of the widest dimension (w). The same oblong character can also be seen in each of the pellets (45-49) of FIGS. 6 & 7, which are all preferred oblong variations (45-49) of pellets (40).

FIGS. 6 & 7 show five representative sample pellets (45-49) representing a particularly preferred embodiment of the preferred oblong variations of pellets (40) of the present invention. As will be elaborated further herein, the pellets (45-49) are preferably formed by polishing metal pellets or shot (preferably formed of aluminum) acquired in raw form from metal fabricators. Referring to the preferred embodiments of FIG. 1, such polished pellets (represented by samples 45-49 in FIGS. 6 & 7) serve as the pellets (40) for thermal bath system (20) in presently preferred embodiments. Because of the shape, thermal conductivity and small size of such pellets (45-49), the particulate media (40) allows for efficient thermal communication by maximizing surface-to-surface contact between the pellets (40) and both the introduced specimen vessel(s) (50) as well as the thermal element (32).

Although oblong pellets (40) according to some aspects of the present invention may have a widest dimension (w) as large as thirty millimeters, the bulk of the pellets (40) of the most preferred embodiment have widest dimensions (w) of less than ten millimeters and preferably more than two millimeters.

In practice, in order to manage costs, the thermally-conductive pellets (40) of preferred embodiments are formed from irregularly-shaped particles of raw material, preferably with rounded and smooth surfaces. Even though such raw material is available with fairly smooth surfaces in its raw state, for optimal use of the present invention, it should be polished smooth in order to minimize friction between adjacent pellets (40) in a bath system (20). Pellets (40) are made of thermally conductive raw material, preferably a solid metal and most preferably aluminum or an aluminum alloy. Such raw material is preferably acquired from metal manufacturing plants in the form of pellets or shot, which may also be referred to as "granny pea," "mini pea" or "granulated particle ingot," and can be obtained at high purity, preferably of greater than 99% purity. The raw material is preferably not molded, in order to minimize cost of manufacture and/or purchase. Any standard small metal parts finishing equipment such as a vibratory bowl or vibratory tub can be used to polish the raw material with or without abrasives to achieve the desired polished surface characteristics of the preferred embodiments.

The performance characteristics of the resulting thermally-conductive pellets (40) are favorable attributes of the preferred embodiments. Not only do the resulting pellets (40) allow for high thermal conductivity and thermal retention when used in system (20), but pellets (40) also provide a balance of mechanical fluidity and support. The balance of mechanical fluidity and support allows vessels (50) to be readily inserted into the particulate media (40) [or the multi-phase media (71), when used in any particular embodiment] and thereafter held in place in a static position due to the mechanical interaction between the particulate media (40). A favorable aspect of the particulate media (40) resulting from this preferred method is that the bulk (i.e., the majority by volume) of the pellets are oblong in shape, which enhances the overall fluidity of the resulting media (40). Moreover, the pellets (40) of preferred embodiments are microbial resistant and are both moisture and gas impermeable.

Although some embodiments use pellets (40) of uniform sizes, other preferred embodiments use pellets (40) of mixed sizes and shapes, which typically allows for improved fluidity and thermal conductivity due to the distribution of smaller pellets with respect to larger pellets in a mixture. Irregularly shaped thermally-conductive pellets (40) preferably have widest dimensions (w) in the range of 2-10 millimeters and preferably take on an overall form of smooth symmetrical or nonsymmetrical ellipsoids, such as in a blend from which the five representative samples of FIGS. 6 & 7 have been sampled.

Despite the general preference to use rounded pellets that have been polished smooth, some aspects of the invention may still be appreciated with less-preferred alternative forms for pellets (40), that may include rough, jagged, uneven, rutted, bumpy, pitted, and etched forms, including polygons such as cubes, cones, pyramids, and cylinders, or twists, or rings, or various combinations of these or other forms.

Figure 8:
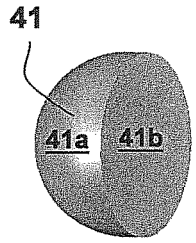
FIG. 8 is a perspective cross-sectional view of a homogenous variation of pellet (41) of certain embodiments of the present invention, which is representative of homogenous variations of each differently-shaped embodiment (41-49) of thermally-conductive pellets (40).

FIG. 8 shows a solid, homogenous pellet (41) as a representative comparator for any of the solid, homogenous pellets (40-49) described above with reference to FIGS. 1-8. As a homogenous pellet (41), the outer surface (41a) is of the same composition as the core (41b) of the pellet (41) shown in FIG. 8, the composition being thermally-conductive and preferably a solid metal. The specific composition of the thermally-conductive material in preferred embodiments is most preferably aluminum or an alloy of aluminum. In alternative embodiments, copper, graphite, cobalt oxide or other thermally-conductive materials may alternately be used as the thermally-conductive raw material for pellets (40), as will be known to those of skill in the art. Alternative materials such as lightweight thermally-conductive plastics, epoxies and the like are particularly advantageous alternatives for use in applications where either minimal weight is desired and/or where there is a desire to minimize electrical conductivity through the particulate thermal media (40) within tub (30).

Figure 9:
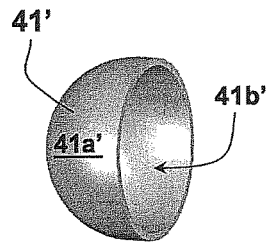
FIG. 9 is a perspective cross-sectional view of a hollow variation (41') of pellet (41) of certain embodiments of the present invention, which is representative of hollow variations of each differently-shaped embodiment (41-49) of thermally-conductive pellets (40).
Figure 10:
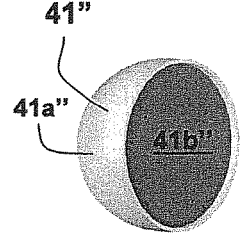
FIG. 10 is a perspective cross-sectional view of a differentially-composed version (41") of pellet (41) of certain embodiments of the present invention, having different surface and core materials, which is representative of differentially-composed variations of each differently-shaped embodiment (41-49) of thermally-conductive pellets (40).

With reference to FIGS. 9 & 10, certain additional advantages are obtained with alternative embodiments that employ pellets (40) having hollow and/or differential composition, respectively. FIG. 9 more particularly shows a representative thermally-conductive pellet (41) having a thermally conductive outer surface (41a') surrounding a substantially hollow core (41b'). FIG. 10 shows a representative thermally-conductive pellet (41) having a thermally conductive outer surface (41a") surrounding a less dense or less conductive core (41b"). The outer surface (41a") can be made from any sufficiently thermally-conductive material and is composed of a different material than the material of inner core (41b"), which can be made from any rigid or non-rigid material such as ceramic, plastic, foam, water, gel or other semi-liquid or liquid. Due to the difference between the thermal conductivity and/or density properties of the surface (41a") and the core (41b") of representative pellet (41"), pellet (41") is referred to as having "differential composition". As will be understood by those of skill in the art, any of the variously shaped pellets (40-49) described in this application can be made of hollow or differential composition just as pellet (41') is hollow and pellet (41") has differential composition.

With reference again to FIG. 1, in some preferred embodiments, tub (30) is filled with a multi-phase media (71), which is a multi-phase variation of thermally-conductive media. Multi-phase media (71) is "multi-phase" in that it is a combination of particulate media (40) and a fluid (70), preferably a liquid. Alternate embodiments of the fluid (70) of multi-phase media (71) include semi-liquids, gasses or vapors, or combinations thereof or combinations with liquids. Preferably, though, multi-phase media (71) includes particulate thermal media (40) [most preferably like oblong pellets (45-49)] together with water or other liquid media (70). In such embodiments, the fluid media (70) is generally included to help enhance the thermal properties of the thermal media (71). Liquid media (70) may also consist of or include lubricants and/or disinfectants (or the like) for the purposes of increasing fluidity and microbial control, respectively, of the media (71) within tub (30).

With embodiments relating to multi-phase media (71) that include liquid fluid media (70), the liquid portion (70) of the thermal media (71) generally fills the interstitial spaces (40') between the pellets (40), at least up to the level of the upper surface (70') of liquid media (70). For embodiments with liquid media (70), the level of the upper surface (referred to as the "fill level")(70') of liquid media (70) preferably covers substantially all of the particulate media (40), such as illustrated in FIG. 1. However, lower liquid fill levels may also be used as desired. For instance, the fill level of liquid media (70) can be limited to a low level (70")(shown in dashed line) that covers the thermal element 32 but does not cover all the particulate media (40). At such a low fill level (70"), thermally-conductive liquid fluid media (70) helps facilitate heat transfer between thermal element (32) and particulate media (40) without wetting as much of the particulate media (40) and/or the specimen vessel(s) (50).

Although not essential to all aspects of the present invention, some preferred embodiments also utilize an impeller (75) (or a tumbler or the like) to stir or agitate the beads (40) and cause them to be specially redistributed within tub (30), thereby increasing the rate of heat transfer within media (40) relative to thermal source (32). Operation of impeller (75) is especially beneficial to rapidly change (or "ramp up" or "boost") the temperature of the particulate media (40) near the top of tub (30), such as may be desired during prep time before vessels (50) are placed in media (40). However, as is shown in FIG. 1, impeller (75) is preferably disposed at a position within tub (30) such that impeller (75) is not likely to physically engage vessel(s) (50) during its operation. As a substitute or augmentation for impeller (75), alternative devices or systems for stirring or otherwise specially redistributing pellets (40) and/or for rapidly boosting or changing the temperature of particulate media (40) will be evident to those of skill in the art. A heated air blower (such as a hair blow dryer) positioned to blow through the media (40) is one particular example of such an alternative embodiment for use to rapidly boost the temperature of particulate media (40), particularly for when media (40) is used dry. Systems for circulating super-heated steam through dry particulate media (40) can also be used to serve both the boost function as well as the sterilization purpose described elsewhere herein. Although not shown in FIG. 1, those of ordinary skill in the art will understand that impeller (75) (or its alternatives or equivalents) has an associated motor and motor controls for turning the shaft (76) to operatively rotate impeller (75).

Despite the benefits of such multi-phase media (71), other aspects of the present invention can be appreciated without using any fluid portion (70) of the thermal media in tub (30), in which cases the particulate media (40) is dry particulate media. By using dry particulate media (40), many of the hazards and maintenance burdens of using water baths can be avoided.

While numerous variations on the size, shape and composition of the particulate media (40) and/or multi-phase media (71) have been described above, it should be understood by those skilled in the art having the benefit of this disclosure that the drawings and detailed description herein are to be regarded in an illustrative rather than a restrictive manner, and are not intended to limit the invention to the particular forms and examples disclosed. On the contrary, the invention includes any further modifications, changes, rearrangements, substitutions, alternatives, design choices, and embodiments apparent to those of ordinary skill in the art, without departing from the spirit and scope of this invention, as defined by the claims that may appear with this application or may be later added or amended. Thus, although the foregoing embodiments have been described, those of ordinary skill in the art will recognize many possible additional alternatives. For example, although it is preferred that at least the bulk of the particulate media (40) consist of a blend or mixture of one or more of the embodiments described herein, it may be beneficial to use particulate media (40) and/or multi-phase media (71) that includes blends or mixtures of the various embodiments that have been described together with other materials that have not been remotely described or even suggested. In any case, all substantially equivalent forms of particulate thermal media should be considered within the scope of the thermal media of this invention to the extent that the claims do not preclude as much when properly construed.

Figure 12:
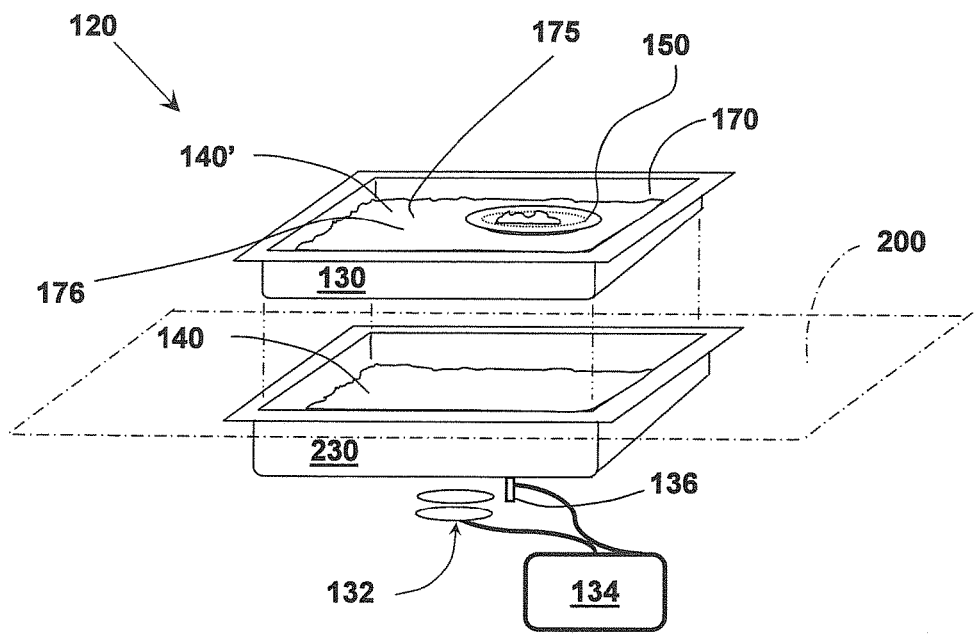
FIG. 12, showing deep pans partially filled with media, illustrates alternate embodiments of the present invention.

With reference to FIG. 12, in some embodiments, a deep pan like pan (130) or pan (230) is used to hold the thermal media. Pan (230) has a shape much like that of a common food service tray and may be installed in a surface such as a tabletop or countertop (200). Like FIG. 1, FIG. 12 shows a heating element (132) energized by a power source (134) and controlled by temperature control until (136), which functions to heat pan (230) and its media (140). One or more objects (150) may be placed on the thermal media (140).

Figure 11:
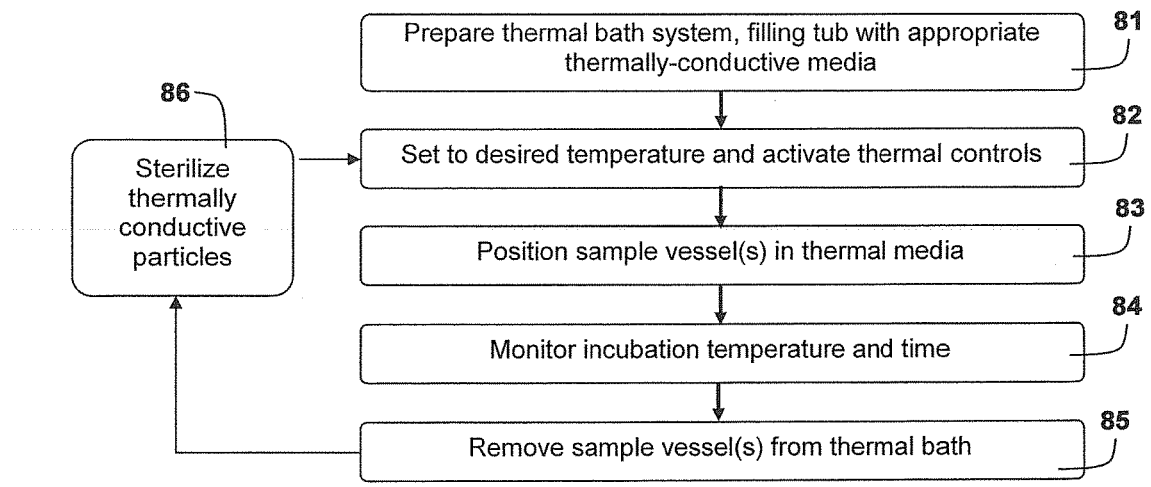
FIG. 11 is a flow chart of a preferred process of using thermally-conductive pellets (40) in a bath system (20) of certain embodiments of the present invention.

While much of the above descriptions describe preferred forms of particulate media (40) and production and preparation of the same, FIG. 11 shows a flow chart of a preferred process of using the thermally-conductive particulate media (40) in a bath system (20) of certain preferred embodiments of the present invention. The first step (81) of such process is to prepare the thermal bath system (20) in accordance with the foregoing descriptions, filling tub (30) with appropriate particulate thermally-conductive media (40) or multi-phase media (71) to the desired fill levels. After preparing and/or obtaining a thermal bath system (20) with thermally-conductive pellets (40) of appropriate character according to the teachings of the present invention, a user (or an automated control) would then proceed to the following steps (82-86).

Referring to the flow chart in FIG. 11, the second step (82) of the preferred process involves setting the system (20) to the desired temperature and activating the thermal controls to maintain as much, thereby bringing the thermal media within tub (30) to the desired temperature, whether it be above or below ambient. Such setting and activating step (82) involves use of thermal source (32), power source (34), and temperature control unit (36) in the conventional manner, with the aid of thermal insulation (38). To shorten the time to reach the desired temperature, it may be appropriate to stir the particulate media (40) after 10-30 min and/or periodically. Once stirred, the temperature of the particulate media (40) should be allowed to equilibrate for 15-60 minutes.

The next step (83) of positioning sample vessel(s) (50) in the thermal media (40, 71) is generally performed manually and is enabled by the fluidity of the particulate media (40). As is conventional with water baths, the objects or specimen vessel(s) (50) should be placed such that they are substantially immersed in media (40) without being immersed so far as to risk contamination through any upper opening in the vessel(s) (50), particularly when a liquid (70) is used with particulate media (40). Once appropriately placed, the vessel(s) (or objects) (50) can then remain in place without a rack and are left to incubate (i.e., to remain at the set temperature) for whatever period of time is desired. After the desired incubation time has been achieved, the vessel(s) (50) are removed (typically by hand) from system (20) at the bottom step (85) for further processing outside of system (20).

The final step (86) before reusing the system (20) is to clean or sterilize the thermally conductive media (40, 71) using techniques mentioned elsewhere herein or as will be evident to those of skill in the art. The final step (86) also preferably involves briefly agitating the particulate media (40) both after the last use and before the next use of system (20). While this step (86) is shown serially between the sample removal step (85) and the restart step (82), it should be understood that sterilization (86) (and other steps) may be omitted entirely or may be performed in a different sequence. This is particularly the case with the sterilization and/or cleaning step (86) as alternative cleaning and/or sterilization processes may be performed during the course of other steps (81-85) of the process, or may be omitted entirely, to the extent that bioburdens within media (40) are within levels required for integrity of whatever test is being conducted on vessel(s) (50).

In a particularly preferred variation of the thermal bath system (20) shown in FIG. 1, programming controls are included with temperature control unit (36) to also control the staged and timed operation of each step (81-86) of the method of FIG. 11. In such variation, control unit (36) includes one or more timers to automatically activate parts of steps (81-86) at scheduled or anticipated times during the day and during each cycle of using system (20). Particularly, automated cleaning and/or sterilizing variations of step (86) are automatically activated by control unit (36) at scheduled times after and before each shift in which the thermal bath system (20) has been or is likely to be used, in order to minimize microbial contamination in tub (30). Likewise, the thermal source (32) and/or the impeller (75) are activated by control unit (36) at scheduled or anticipated times before each shift in which the thermal bath system (20) is likely to be used, in order to minimize costly staff and/or equipment downtime (and potentially costly waste of specimens) while waiting for the required temperature of media (40) to be reached. Once the required temperature of media (40) is attained, as determined by a temperature probe or the like connected to control unit (36), automated controls in unit (36) then preferably deactivate impeller (75) and cause a visual, auditory or electronic "READY" signal to be presented to users of system (20). Thereafter, thermal controls continue to maintain the temperatures in the conventional manner, allowing for a user to program the duration of the incubation time (or the remaining incubation time) or to adjust the temperature setting of control unit (36) to any particular level at any time. Once the programmed incubation time is completed, the automated controls of unit (36) preferably also include provision for presenting an "INCUBATION COMPLETE" visual, auditory or electronic signal to indicate that the desired incubation period is completed, while also discontinuing operation of thermal source (32) at the appropriate time.

In certain embodiments, such automated controls of control unit (36) may also be coupled to automated specimen racks in order to cause vessel(s) (50) to be inserted into and/or removed from media (40) in accordance with a pre-programmed sequence, in order to provide a fully automated system (20).

In broad embodiment, the present invention is thermal bath media of thermally-conductive particulate media of any shape or material which can be used to replace conventional wet or dry media in existing laboratory thermal bath for transferring thermal energy to objects placed within. The present invention also envisions laboratory thermal bath optimally designed for use with thermally-conductive particulate media. Such laboratory thermal baths can comprise tub designs that provide optimal containment of the thermal bath media, optimal thermal transfer properties, and optimal design for ease-of-use, adaptation to robotic platforms and sterile laboratory applications.

While the foregoing written description enables one of ordinary skill to make and use what is considered presently to be the best mode thereof, those of ordinary skill will understand and appreciate the existence of variations, combinations, and equivalents of the specific embodiment, method, and examples herein. The invention should therefore not be limited by the above described embodiment, method, and examples, but by all embodiments and methods within the scope and spirit of the invention as claimed. It is intended instead that any claims with this application, or any claims that may be added or amended, be interpreted to embrace all further modifications, changes, rearrangements, substitutions, alternatives, design choices, and embodiments that may be evident to those of skill in the art. Although the foregoing embodiments are the most preferred at present, those of ordinary skill in the art will recognize many possible alternatives. For example, it may be possible to find another material that works better than the particulars we have discussed. In any case, all substantially equivalent systems, articles and methods should be considered within the scope of the present invention.

I claim:

1. A thermal control system for controlling the temperature of a sample in a vessel, comprising:
   (a) a thermal bath having a tub and a thermal source; and
   (b) thermally-conductive media comprising thermally-conductive pellets within said tub in thermal communication with said thermal source; said pellets having a thermally-conductive composition; said pellets being comprised of a plurality of oblong metal pellets; said pellets being comprised of metal selected from the group consisting of aluminum, silver, and copper; and said pellets being polished and said thermally-conductive media being positioned in said tub in a manner such that one or more sample vessels can be inserted within said media in thermal communication with said media.

2. A thermal control system for controlling the temperature of a sample in a vessel, comprising:
   (a) a thermal bath having a tub and a thermal source; and
   (b) thermally-conductive media comprising oblong pellets within said tub in thermal communication with said thermal source; said oblong pellets having a thermally-conductive composition; said oblong pellets being comprised of aluminum;
   and said oblong pellets being polished and said thermally-conductive media being positioned in said tub in a manner such that one or more sample vessels can be inserted within said media in thermal communication with said media.

3. The thermal control system of claim 2, wherein said oblong pellets are comprised of a plurality of oblong metal pellets having a widest dimension of more than two, but not more than thirty, millimeters.

4. The thermal control system of claim 2, wherein said thermal bath comprises a laboratory thermal bath.

5. The thermal control system of claim 2, further comprising a supply of antimicrobial compound for decontaminating the surface of said oblong pellets.

6. The thermal control system of claim 5, wherein said antimicrobial compound comprises a liquid periodically applied to said surface of said oblong pellets.

7. The antimicrobial compound of claim 6, wherein the liquid comprises silver.

8. The antimicrobial compound of claim 6, wherein the liquid comprises aluminum.

9. The antimicrobial compound of claim 6, wherein the liquid comprises alcohol.

10. The antimicrobial compound of claim 6, wherein the liquid comprises chlorine.

11. A method for controlling the temperature of a specimen in a vessel in a thermal bath, comprising the steps of: filling said thermal bath with thermally-conductive metal pellets wherein said metal pellets are oblong in shape and have edges that are rounded and surfaces that are polished; inserting said vessel into said pellets after bringing said pellets to a desired temperature; and maintaining said vessel in said pellets for a desired period of time.

12. The method of claim 11, wherein said metal pellets are comprised of a plurality of oblong metal pellets having a widest dimension of more than two, but not more than thirty, millimeters.

13. The method of claim 12, wherein said metal pellets are comprised of metal selected from the group consisting of aluminum, silver, and copper.

* * * * *